United States Patent [19]

White et al.

[11] Patent Number: 4,999,445

[45] Date of Patent: Mar. 12, 1991

[54] CONTRAST AGENTS FOR MAGNETIC RESONANCE IMAGING OF THE SMALL INTESTINE AND HEPATOBILIARY SYSTEM

[75] Inventors: David L. White, Oakland; Barry L. Engelstad, Orinda; Kurt A. Muetterties, Oakland, all of Calif.

[73] Assignee: The Regents of the University of California, Oakland, Calif.

[21] Appl. No.: 205,201

[22] Filed: Jun. 10, 1988

[51] Int. Cl.$^5$ .............................................. C07F 15/02
[52] U.S. Cl. ...................................... 556/138; 556/1; 556/45; 534/15
[58] Field of Search ................. 556/45, 1, 138; 424/9, 424/1.1; 514/502, 449, 451; 534/15

[56] References Cited

U.S. PATENT DOCUMENTS 4,758,422  7/1988  Quay ....................................... 424/9

Primary Examiner—Arthur C. Prescott
Attorney, Agent, or Firm—Flehr, Hohbach, Test, Albritton & Herbert

[57] ABSTRACT

A method is provided utilizing contrast agents which provide increased diagnostic information in the magnetic resonance image of the hepatobiliary system and alimentary tract, especially the small intestine. Novel contrast agents which are N-carboxylated desferrioxamine B complexes with metal ions are provided.

4 Claims, No Drawings

CONTRAST AGENTS FOR MAGNETIC RESONANCE IMAGING OF THE SMALL INTESTINE AND HEPATOBILIARY SYSTEM

The present invention is directed to a novel class of carboxylic acid derivatives of the iron (III) chelate of desferrioxamine B which are useful as magnetic resonance imaging contrast agents for renal, hepatobiliary and, in particular small intestine image enhancement.

This invention was made with Government support under Grant No. CA38918 awarded by the Department of Health and Human Services. The Government has certain rights in this invention.

BACKGROUND OF THE INVENTION

The iron (III) chelate of desferrioxamine B is a known magnetic resonance imaging contrast agent that gives both renal and hepatobiliary enhancement. It is one of the soluble paramagnetic compounds used for this purpose. Other soluble paramagnetic compounds, such as Gd-DTPA, suffer from various disadvantages, such as, rapid diffusion from the vascular system into the extracellular space, lack of specificity for liver and essentially no concentration in the bile. Manganese dichloride concentrates in the liver after IV injection, is transported to the bile and excreted in the feces, however, it is toxic and is not practically useful in a clinical situation. Iron (III) complexes Fe-EHPF and Fe-HBED are useful contrast agents in the liver and are secreted into the bile. However, their appearance in the bile does not take place until approximately 20 minutes post injection and furthermore, enhancement of the lumen of the small intestine is seldom observed using these agents.

The magnetic resonance imaging of the gastrointestinal tract is limited by inherently low image contrast, motion and variable anatomic appearance. Agents for this purpose are normally administered orally and reside within lumen of the GI tract to provide either positive (increased signal strength) or negative (decreased signal strength) contrast. In the usual situation, positive contrast is provided by ingestion of paramagnetic agents such as Gd-DTPA or iron citrate while negative contrast is provided by displacement of the luminal proton-containing contents by gas (such as carbon dioxide from gas tablets) or perfluorocarbons. Negative contrast can also be obtained by ingestion of ferromagnetic or superparamagnetic particles, such as ferrite.

There is thus a need in the art for MRI contrast agents which are useful both for hepatobiliary studies and for gastrointestinal studies, particularly when introduced by intravenous administration, rather than by oral administration.

It is thus an object of the present invention to provide improved desferrioxamine B contrast agents for magnetic resonance imaging.

It is yet another object of the present invention to provide magnetic resonance imaging contrast agents having high stability, low toxicity, physiological tolerability and which provide for positive imaging of the small intestine rapidly after intravenous administration.

It is a further object of the present invention to provide desferrioxamine B contrast agents which are organ selective.

SUMMARY OF THE INVENTION

Briefly, these and other objects of the present invention are accomplished by providing chemically stable physiologically tolerable desferrioxamine B derivatives for in vivo use for MRI imaging. The present invention provides a method for performing magnetic resonance imaging diagnostic procedures in a subject comprising administering intravenously to the subject a magnetic resonance imaging enhancement effective amount of a diagnostic medium comprising the compound of the following formula in a physiologically acceptable carrier:

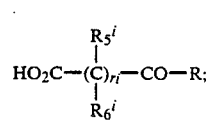

wherein R is -desferrioxamine B; i is an integer from 1 to r; r is an integer from 2 to 18; and each $R_5^i$ and $R_6^i$ is independently hydrogen, aryl of 6 to 14 carbon atoms, or substituted aryl having at least one substituent selected from the group consisting of halo, alkyl of 1 to 6 carbon atoms, nitro, sulfonyl, hydroxyl, alkoxy of 1 to 6 carbon atoms, carboalkoxy of 2 to 6 carbon atoms, alkoxycarbonyl of 2 to 6 carbon atoms and sulfhydryl.

DESCRIPTION OF THE PREFERRED EMBODIMENTS

Media according to the present invention are useful for magnetic resonance imaging diagnosis. Production of the diagnostic media according to the present invention may be performed according to ways known in the art, i.e., by forming a complex salt as described hereinbelow, optionally with the addition of customary additives such as galenicals, which may be suspended or dissolved in an aqueous medium followed by sterilization. Suitable additives include, for example, physiologically biocompatible buffers such as tromethamine hydrochloride, complexing agents such as diethylenediiaminepentaacetic acid, or if necessary electrolytes such as sodium chloride.

The compounds according to the present invention which are utilized in the present method are those of the following formula

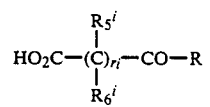

wherein R is desferrioxamine B and $R_6^i$ and $R_5^i$ are as described hereinabove. In the compounds according to the present invention the radical desferrioxamine B is of the following formula

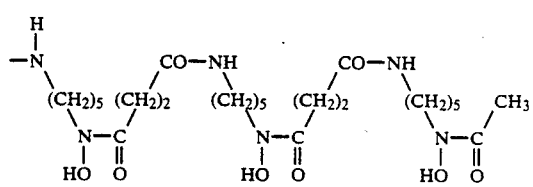

and is complexed with a paramagnetic ion.

The active ingredient of the contrast agents according to the present invention are generally prepared by treating a salt of desferrioxamine B, such as the mesylate, with an appropriate anhydride of a dicarboxylic acid. By using two or more equivalents of the anhydride to one equivalent of the protected desferrioxamine B, in a basic medium, the primary amino group of the desferrioxamine B will react with the anhydride and form an N-carboxylate desferrioxamine B derivative. Any —O— esters that may have formed during the amidation reaction may then be removed under conventional conditions to result in the N-carboxylated desferrioxamine B contrast agents according to the present invention. Treatment of the anhydride with desferrioxamine B will normally be conducted at around 100° to 110° C., in a suitable solvent, such as pyridine. Treatment of the ligand with an appropriate metal salt of the desired metal counterion will form the metal complex. Alternatively, the N—OH groups may be protected by esterification or by complexation with a metal ion.

The preferred iron (III) complex of the N-carboxylated desferrioxamine B compound may be prepared by treatment thereof with ferric chloride in an acidic aqueous medium, followed by basification to a pH of about 7.5 to 8.

Particularly preferred contrast agents according to the present invention are the N-(glutaramido), N-(succinamido) and N-(3-phenylglutaramido) desferrioxamine B complexes with iron (III). In particular, the N-(3-phenylglutaramido) desferrioxamine B iron (III) complex is advantageously used for MRI imaging of the small intestine. In addition, certain of the N-carboxylated desferrioxamine B ligands and complexes thereof with metals according to the present invention having the following formula are novel.

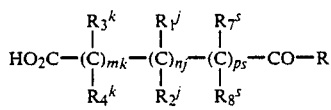

wherein R is -desferrioxamine B; j is an integer from 1 to n; k is an integer from 0 to m; s is an integer from 0 to p; n+m+p is less than or equal to 18; each $R_1{}^j$ is independently aryl of 6 to 14 carbon atoms, or substituted aryl having at least one substituent selected from the group consisting of halo, alkyl of 1 to 6 carbon atoms, nitro, sulfonyl, hydroxyl, alkoxy of 1 to 6 carbon atoms, carboalkoxy of 2 to 6 carbon atoms, alkoxycarbonyl of 2 to 6 carbon atoms and sulfhydryl; and each $R_2{}^j$, $R_4{}^k$, $R_7{}^s$ and $R_8{}^s$ independently hydrogen, aryl or substituted aryl as defined above.

The contrast agents according to the present invention are particularly advantageous in that upon intravenous injection, they concentrate in bile, and in some cases, appear in the small intestine very rapidly, usually within about two minutes post injection. They are useful in that they may be administered by the intravenous route, thus the entry into the small intestine is by the hepatobiliary system. Therefore, in addition to contrast enhancement of alimentary tract lumen, with its resulting increased anatomical information, the contrast agents also provide functional information. For example, hepatobiliary dysfunctions, such as bile duct occlusion will retard, lessen or prevent the transport of the contrast agent and thus be revealed by MRI. Appearance in the intestinal lumen, usually within two minutes post injection, is particularly advantageous for imaging since the optimum imaging time for the small intestine can thereby be readily predicted. Such timing is extremely difficult with use of orally administered agents for MRI of the small intestine. The contrast agents according to the present invention not only show specificity for the biliary system and small intestines, but they also are relatively non-toxic and substantially completely excreted. Conventional hepatobiliary contrast agents, such as Gd-DTPA, distribute in the extracellular volume and are not useful therefore for imaging the small intestine.

The reagents according to the present invention therefore can reveal additional details regarding the anatomy of the small intestines, and because of their very rapid localization in the bile and gut lumen, the MRI of these organ systems are simplified and thereby expedited.

It will be appreciated that other metal ions besides iron (III) may be utilized to complex with the ligands according to the present invention for use in magnetic resonance imaging. Useful metal ions include Dy (III), Gd (III), Cr (III), and Mn (II).

The agents according to the present invention are utilized preferably in solutions made by addition of a solvent such as water, serum, albumin solutions, or saline to the complex. A typical injectable composition will contain about 10 mg/ml human serum albumin with a metal complex concentration of about 20 to 200 mg/ml. A 0.1 m phosphate buffer (7.5 pH) may be employed containing, for example, about 0.9% sodium chloride. The pH of the aqueous solutions may range between about 5 to 9 over a volume range of about 5 to 150 ml. This viscous diagnostic reagent may then be injected into a subject usually in an amount of 0.001 to 5 mmole of contrast agent, and the subject may then be imaged by a conventional magnetic resonance imaging system. Typical imaging systems are disclosed, for example, in *Scientific American*, May 1982, pp. 78–88, and "NMR: A Primer For Medical Imaging" by Wolf and Popp, Slack Book Division (ISBN 0-943432-19-7), which are incorporated herein by reference.

The following examples are provided by way of illustration of the invention but are not in any way intended to limit the invention.

EXAMPLE 1

Preparation of 3-Phenylglutaric Anhydride

3-Phenylglutaric anhydride, 5.0 g (24 mmoles), was dissolved in 25 ml of dry acetic anhydride, and the resulting solution was heated to 100° C. and stirred for 3 hours. The reaction mixture then was allowed to cool to 35° C. and held at that temperature for 1.5 hours. Removal of the acetic anhydride using a rotary evaporator, and recrystallization of the resulting crude solid from chloroform gave 2.25 g (11.8 mmoles; 50% of theory) of the title compound, mp. 102°–103° C.

EXAMPLE 2

Preparation of N-(-phenylglutaramido)desferrioxamine

To 1.5 g (2.28 mmoles) of desferrioxamine B mesylate in 30 mL of pyridine was added 0.85 g (4.47 mmoles) of 3-phenylglutaric anhydride. The resulting solution was stirred for 2 hours at 110° C., cooled to 55° C., and then held at that temperature for 18 hours. Then 30 ml of 2N aqueous ammonia was added to the reaction mixture, and it was stirred for 15 minutes at ambient temperature.

Pyridine was removed from the reaction mixture by extraction with dichloromethane. The aqueous fraction then was striped to dryness using a rotary evaporator. The resulting solid residue was redissolved in 40 ml of water, and this solution was acidified to pH 2-2.5 by the addition of 1N HCl. After acidification, the solution was filtered, and the filtrate was treated with an equivalent volume of acetone. Cooling of this solution afforded 1.29 g (1.72 mmoles; 75% of theory) of white solid, mp. 123.5°–126° C. Anal. Calc'd for $C_{36}H_{58}N_6O_{11}$:C, 57.60; H, 7.73; N, 11.20. Found: C, 57.39; H, 7.59; N, 11.2. Mass spectrum (LSIMS): $(M+H)^+ = 751$; $(M+Na)^+ = 773$.

EXAMPLE 3

Preparation of N-(Glutaramido)desferrioxamine B

N-(glutaramido)desferrioxamine B was prepared similarly using 1.41 g (12.37 mmoles) of glutaric anhydride and 4.91 g (7.47 mmoles) of desferrioxamine B mesylate. Recrystallization from dilute HCl (pH 2.5) gave 3.08 g (4.6 mmoles, 62% of theory) of white solid, mp. 154°–158° C. Anal. Calc'd for $C_{30}H_{54}N_6O_{11}$: C, 53.41; H, 8.01; N, 12.46. Found: C, 53.29; H, 7.88; N, 12.37. Mass spectrum (LSIMS): $(M+H)^+ = 675$; $(M+Na)^+ = 697$.

EXAMPLE 4

Synthesis of N-(succinamido)desferrioxamine B

N-(succinamido)desferrioxamine B was prepared similarly to the glutaric derivative using 0.68 g (6.8 mmoles) of succinic anhydride and 2.0 g (3.0 mmoles) of desferrioxamine B mesylate. Recrystallization from dilute HCl (pH 2.5) gave 0.72 g (1.1 mmoles, 37% of theory) of white solid, mp. 152°–154° C. Anal. Calc'd for $C_{29}H_{52}N_6O_{11}$: C, 52.71; H, 7.93; N, 12.72. Found: C, 52.5; H, 7.9; N, 12.4. Mass spectrum (LSIMS): $(M+H)^+ = 661$; $(M+Na)^+ = 683$.

EXAMPLE 5

Preparation of the Fe(III) Complex of N-(3-phenylglutaramido)desferrioxamine (Fe-PGDF)

To 160 mg (12 mmoles) of imidoacetic acid dissolved in 1 ml of aqueous NaOH (pH=8), was added 134 mg (5 mmoles) of FeCl₃ 6 H₂O. This solution was brought to pH=8 with 2N NaOH, and to it was added 375 mg (5 mmoles) of N-(3-phenylglutaramido)desferrioxamine (PGDF) dissolved in 1 mL of water. The resulting mixture was adjusted to pH−7.5 with 2N NaOH, and filtered through a 0.2 um filter to yield a red solution of the Fe III) complex. After appropriate dilution with water, this material was used for in vivo imaging experiments.

EXAMPLE 6

A normal, male Sprague-Dawley rat was anesthetized with 50 mg/kg i.p. sodium pentobarbital and fitted with a tail-vein catheter. The animal was then placed in an imaging coil, and the coil plus animal was inserted into the magnet bore of a General Electric Model CSI-II Magnetic Resonance Imager/Spectrometer. Non-gated spin-echo images were acquired using TR and TE equal to 320 and 15 msec, respectively. Following these pre-contrast images, 0.52 mL of a 0.10 M Fe-PGDF solution was injected, and images were acquired at various time intervals post injection. Within one minute of injection the liver, stomach and small intestine showed enhanced contrast, particularly the small intestine. One hour post injection contrast enhancement of the urinary bladder began with the contrast enhancement of the small intestine being diminished. Several hours post injection showed only enhancement of contrast in the urinary bladder.

What is claimed is:

1. A metal complex comprising a metal ion selected from the group consisting of Fe(III), Dy(III), Gd(III), Cr(III) and Mn(II) and a ligand of the formula

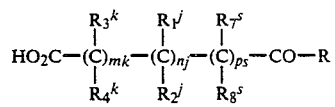

wherein R is -desferrioxamine B; j is an integer from 1 to n; k is an integer from O to m; s is an integer from O to p; p+n+m is less than or equal to 18; each $R_1{}^j$ is independently aryl of 6 to 14 carbon atoms, or substituted aryl having at least one substituent selected from the group consisting of halo, alkyl of 1 to 6 carbon atoms, nitro, sulfonyl, hydroxyl, alkoxy of 1 to 6 carbon atoms, carboalkoxy of 2 to 6 carbon atoms, alkoxycarbonyl of 2 to 6 carbon atoms and sulfhydryl; and each $R_2{}^j$, $R_3{}^k$, $R_4{}^k$, $R_7{}^s$ and $R_8{}^s$ is independently hydrogen, aryl or substituted aryl as defined above.

2. A metal complex according to claim 1 wherein R is

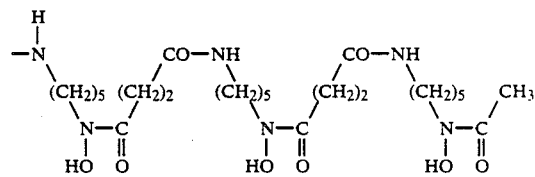

and said metal is iron (III).

3. A complex according to claim 2 wherein n=1, m=1 and p=1; R₈, R₇, R₂, R₃ and R₄ are all hydrogen and R₁ is phenyl.

4. A complex according to claim 1 wherein p=1, n=1 and m=1; and R₁, R₂, R₃, R₄, R₇ and R₈ are all hydrogen.

* * * * *